US011077308B2

(12) United States Patent
Opris et al.

(10) Patent No.: US 11,077,308 B2
(45) Date of Patent: Aug. 3, 2021

(54) HIGHLY ACCURATE TEMPERATURE SENSORS, AND CALIBRATIONS THEREOF, FOR USE WITH IMPLANTABLE MEDICAL DEVICES

(71) Applicant: Pacesetter, Inc., Santa Clara, CA (US)

(72) Inventors: Ion Opris, San Jose, CA (US); Dean Andersen, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 411 days.

(21) Appl. No.: 16/171,103

(22) Filed: Oct. 25, 2018

(65) Prior Publication Data

US 2020/0129770 A1   Apr. 30, 2020

(51) Int. Cl.
| G01K 7/00 | (2006.01) |
| A61N 1/37 | (2006.01) |
| A61N 1/39 | (2006.01) |
| G01K 7/01 | (2006.01) |
| G01K 15/00 | (2006.01) |

(52) U.S. Cl.
CPC ......... A61N 1/3706 (2013.01); A61N 1/3925 (2013.01); A61N 1/39622 (2017.08); G01K 7/01 (2013.01); G01K 15/005 (2013.01)

(58) Field of Classification Search
CPC combination set(s) only.
See application file for complete search history.

(56) References Cited

U.S. PATENT DOCUMENTS

| 8,446,140 | B2 | 5/2013 | Harvey |
| 9,261,415 | B1* | 2/2016 | Zhang ................. G05F 3/16 |
| 9,748,969 | B1* | 8/2017 | Bach ................ H03M 3/382 |
| 2005/0075682 | A1 | 4/2005 | Schulman et al. |
| 2007/0091979 | A1 | 4/2007 | Chiu |
| 2010/0111137 | A1 | 5/2010 | Chen et al. |
| 2011/0200070 | A1* | 8/2011 | Makinwa ............ G06K 19/0723 374/170 |
| 2012/0326693 | A1 | 12/2012 | Marten |

(Continued)

OTHER PUBLICATIONS

Pertijs, et al., "A CMOS Smart Temperature Sensor With a 3σ Inaccuracy of +/−0.1° C From -55° C to 125° C", IEEE Journal of Solid-State Circuits, vol. 40, No. 12, Dec. 2005, pp. 2805-2815.

(Continued)

Primary Examiner — Lisa M Caputo
Assistant Examiner — Nasir U. Ahmed
(74) Attorney, Agent, or Firm — Vierra Magen Marcus LLP

(57) ABSTRACT

Certain embodiments of the present technology relate to temperature sensors for using in an implantable medical device, and methods for use therewith. Such a method can include alternating between producing a first base-to-emitter voltage drop (VBE1) and a second base-to-emitter voltage drop (VBE2), and alternating between using a capacitor to store the VBE1, which is complimentary to absolute temperature (CTAT), and using the same capacitor to store a ΔVBE=VBE2−VBE1, which is proportion to absolute temperature (PTAT). The method also includes using a sigma-delta modulator that includes the capacitor to produce a signal having a duty cycle (dc) indicative of the ΔVBE stored using the capacitor, and producing a temperature measurement based on the signal having the duty cycle (dc) indicative of the ΔVBE.

23 Claims, 8 Drawing Sheets

(56) References Cited

U.S. PATENT DOCUMENTS

| | | |
|---|---|---|
| 2001/3026149 | 10/2013 | Pertijs et al. |
| 2013/0259091 A1* | 10/2013 | Chen .................. G01K 7/34 |
| | | 374/184 |
| 2014/0084899 A1 | 3/2014 | Powell et al. |
| 2014/0140364 A1* | 5/2014 | Charles ............ G01K 15/005 |
| | | 374/1 |
| 2015/0003490 A1* | 1/2015 | Ash .................... G01K 7/01 |
| | | 374/1 |
| 2015/0369674 A1 | 12/2015 | Ma |
| 2017/0045403 A1* | 2/2017 | Zanbaghi ............ G01K 7/01 |

OTHER PUBLICATIONS

Renesas, "A Brief Introduction to Sigma Delta Conversion", Application Note, AN9504, Rev. 0.00, May 1995, pp. 1-8.

Almeida et al., "CMOS Sigma-Delta Thermal Modulator", 2010 IEEE Instrumentation & Measurement Technology Conference Proceedings, May 2010.

Yixuan Yan, "Voltage Calibration of BJT Based Temperature Sensor", Thesis, Delft University of Technology, 2017, pp. 1-36.

International Search Report & the Written Opinion of the International Searching Authority dated Jan. 23, 2020, International Application No. PCT/US2019/055228.

* cited by examiner

HIGHLY ACCURATE TEMPERATURE SENSORS, AND CALIBRATIONS THEREOF, FOR USE WITH IMPLANTABLE MEDICAL DEVICES

FIELD OF TECHNOLOGY

Embodiments described herein generally related to temperature sensors, and more particularly, temperature sensors for use in implantable medical devices (IMDs), and methods for use therewith.

BACKGROUND

Temperature sensors are utilized for a variety of purposes in implantable medical devices (IMDs). For example, a temperature sensor can be used to sense body temperature for vital signs monitoring and/or diagnostic purposes in an insertable cardiac monitor (ICM). Alternatively, or additionally, an IMD can use a temperature sensor to perform rate-adaptive pacing, e.g., by using the temperature sensor to detect changes in a patient's activity based on changes in the patient's blood temperature. For still another example, a temperature sensor can also be used to measure local heating of circuit components to ensure the circuit components stay within safe limits. This latter example is particularly useful for rechargeable battery systems, which are often included in implantable neurostimulators.

Commercially available temperature sensors are considered to have high accuracy if they provide temperature measurements that are within +/−0.5 degrees Celsius (° C.) of the actual temperature. For body temperature monitoring, it is often desirable that an absolute temperature sensor have an accuracy within at least +/−0.1 degrees of the actual absolute temperature. Assuming a nominal body temperature of 37° C. (which is about 310.15 degrees Kelvin) this represents an error of about 0.03% at the nominal body temperature of 37° C. Explained another way, it is often desirable for body temperature monitoring to be within at least +/−0.03 degrees Celsius of an actual temperature. The actual temperature can be alternatively referred to as the known temperature, and these terms are used interchangeably herein.

Highly accurate temperature sensors typically require calibration at a precisely controlled temperature. Indeed, some highly accurate temperature sensors require calibration at multiple known temperatures to attain a desired accuracy and/or to compensate for undesirably non-linearities. This creates manufacturing challenges in generating the precise temperature(s) and waiting for proper "soaking" time. For best accuracy, it is typically recommended to calibrate temperature sensors for IMDs at or near a nominal body temperature of 37° C.

SUMMARY

Certain embodiments of the present technology relate to temperature sensors for using in an implantable medical device, and methods for use therewith. Such a method can include alternating between producing a first base-to-emitter voltage drop (VBE1) and a second base-to-emitter voltage drop (VBE2), and alternating between using a capacitor to store the VBE1, which is complimentary to absolute temperature (CTAT), and using the same capacitor to store a ΔVBE=VBE2−VBE1, which is proportion to absolute temperature (PTAT). The method also includes using a sigma-delta modulator that includes the capacitor to produce a signal having a duty cycle (dc) indicative of the ΔVBE stored using the capacitor, and producing a temperature measurement based on the signal having the duty cycle (dc) indicative of the ΔVBE.

In accordance with certain embodiments, producing the signal having the duty cycle (dc) indicative of ΔVBE is performed using a sigma-delta modulator that includes the capacitor. More specifically, the sigma-delta modulator includes a summing node, an integrator, a 1-bit quantizer, and a 1-bit digital-to-analog converter (DAC). The summing node is coupled to a terminal of the diode device that alternately produces the VBE1 and the VBE2. The signal having the duty cycle (dc) indicative of the ΔVBE is output by the 1-bit quantizer. Advantageously, the capacitor used to store the ΔVBE is part of both the integrator and the 1-bit DAC of the sigma-delta modulator.

In according with certain embodiments, producing the temperature measurement, based on the signal having the duty cycle (dc) indicative of the ΔVBE, includes filtering the signal having the duty cycle (dc) indicative of the ΔVBE to thereby produce a digital value corresponding to the duty cycle (dc) indicative of the ΔVBE. At least one of a processor, an equation, or a look up table (LUT) is used to produce the temperature measurement based on the digital value corresponding to the duty cycle (dc) indicative of the ΔVBE. In accordance with certain embodiments, the temperature measurement is within +/−0.1° C. of an actual temperature.

In accordance with certain embodiments, the diode device and the capacitor are components of an integrated circuit (IC) temperature sensor. A single calibration temperature measurement is produced using the IC temperature sensor while the IC temperature sensor is in a location having a known temperature, and a single point calibration of the IC temperature sensor is performed using the single calibration temperature measurement. In certain embodiments, the IC temperature sensor is for use within a specified temperature range of interest, and the known temperature (of the location where the IC temperature sensor is located when the single calibration temperature measurement is produced) is outside the specified temperature range of interest, and thus, the single calibration temperature measurement used for the single point calibration is outside the specified temperature range of interest.

In accordance with certain embodiments, alternating between providing the first amount of current and the second amount of current to the same diode device is achieved in the following manner. Each current source, of a group of N current sources, is used to produce a corresponding current that is substantially equal to the currents produced by the other current sources within the group, wherein N is ≥3. Additionally, there is an alternating between connecting one of the N current sources in the group to the diode device to thereby cause the providing of the first amount of current to the diode device, and connecting the N current sources in the group to the diode device to thereby cause the providing of the second amount of current to the diode device. In accordance with certain embodiments, which one of the N current sources is connected to the diode device, to thereby cause the providing of the first amount of current to the diode device, is changed in a round-robin, random, or pseudo-random manner so that small differences in the currents produced by the N current sources are averaged out over time.

Certain embodiments of the present technology are directed to a temperature sensor for use in an implantable medical device, wherein the temperature sensor includes a diode device, a plurality of current sources, a sigma-delta modulator, and a controller. The diode device can be, e.g., a bipolar junction transistor (BJT) having a base, an emitter, and a collector, with the base and the collector connected to one another so that the diode device comprises a diode connected transistor. The controller can be configured to control alternating between providing a first amount of current and a second amount of current produced using the current sources, or subsets thereof, to the diode device, to thereby alternate between producing a first base-to-emitter voltage drop (VBE1) and a second base-to-emitter voltage drop (VBE2) using the same diode device. The sigma-delta modulator includes a capacitor configured to alternate between storing the VBE1, which is CTAT, and storing a ΔVBE=VBE2−VBE1, which is PTAT. The sigma-delta modulator is configured to produce a signal having a duty cycle (dc) indicative of the ΔVBE. In accordance with certain embodiments, the temperature sensor also includes a filter and a scaler. The filter is configured to filter the signal having the duty cycle (dc) indicative of the ΔVBE to thereby produce a digital value corresponding to the duty cycle (dc) indicative of the ΔVBE. The scaler is configured to produce the temperature measurement based on the digital value corresponding to the duty cycle (dc) indicative of the ΔVBE. The scaler can be implemented, e.g., using a processor configured to perform an equation or use a LUT to produce the temperature measurement based on the digital value corresponding to the duty cycle (dc) indicative of the ΔVBE. In certain embodiments, the temperature measurement that is output by the scaler is corrected for non-linearities using a non-linear equation or a look up table, or the like. Such corrections for non-linearities can be performed, e.g., using firmware or software of the implantable medical device, or using firmware or software of a non-implanted external device (e.g., an external programmer) to which the temperature measurement is uploaded, but is not limited thereto.

In accordance with certain embodiments, the sigma-delta modulator includes a summing node, an integrator, a 1-bit quantizer, and a 1-bit DAC. The summing node is coupled to a terminal of the diode device that alternately produces the VBE1 and the VBE2. The signal having the duty cycle (dc) indicative of the ΔVBE is output by the 1-bit quantizer. The capacitor that is used to store the ΔVBE is part of both the integrator and the 1-bit DAC of the sigma-delta modulator. The sigma-delta modulator can be a first order or higher order sigma-delta modulator.

In accordance with certain embodiments, the diode device and the sigma-delta modulator are components of an IC temperature sensor configured to be calibrated using a single calibration temperature measurement obtained using the IC temperature sensor while the IC temperature sensor is in a location having a known temperature that is outside a specified temperature range of interest. In accordance with certain embodiments, the IC temperature sensor is configured to produce the temperature measurement such that it is within +/−0.1° C. of an actual temperature.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Embodiments of the present technology are generally related to temperature sensors, and more particularly, temperature sensors for us in implantable medical devices (IMDs). Ideally a temperature sensor could be calibrated using only one known temperature that does not have to be within the normal temperature range of use (also referred to as the desired range) and still be highly accurate. For the case of an IMD, it would be beneficial to calibrate a temperature sensor at room temperature (e.g., 21° C.) during manufacturing, but still have the temperature sensor be accurate (to at least +/−0.1° C.) within the range of body temperatures (approximately 36° C. to 40° C.).

Certain embodiments of the present technology provide for the flexibility of being able to calibrate the temperature sensor at any normal operation temperature without sacrificing accuracy within the temperature range of interest, e.g., within the range of body temperatures (approximately 36° C. to 40° C.). Such embodiments enable calibration of the temperature sensor during manufacturing at a single temperature point that does not have to be within or even near the range of body temperatures, any time the device is at a room temperature that is accurately known, or after implant when the body temperature is accurately known or can be accurately measured.

Integrated circuit (IC) temperature sensors exploit the relationship between voltage references and temperature. Some voltage references are proportional to absolute temperature (PTAT) and other voltage references are complementary (i.e., inverse) to absolute temperature (CTAT). Most temperature sensors use one type of voltage reference to sense the shift in voltage across temperature. Across wide temperature ranges, this is not particularly challenging, although linearity is. What makes this application challenging is that across a very narrow temperature range (e.g., the range of body temperatures), it is difficult to achieve high accuracy (i.e., low error) in reading the temperature.

As will be described in additional detail below, certain embodiments of the present technology utilize two sources of temperature varying voltages. Both a PTAT voltage reference and a CTAT voltage reference are used to obtain a temperature reading. These voltages are linear with temperature after applying a correction factor. An advantage of this scheme is that both the CTAT voltage reference and the PTAT voltage reference are linear with each other, albeit inversely. Because of this linear relationship, calibrating the temperature sensor at one temperature retains its accuracy at other temperatures, even if the calibration temperature is not near body temperature (i.e., not within the narrow temperature range of body temperatures). The narrow temperature range of body temperatures can be from about 36° C. to about 40° C., as noted above.

Figure 1:
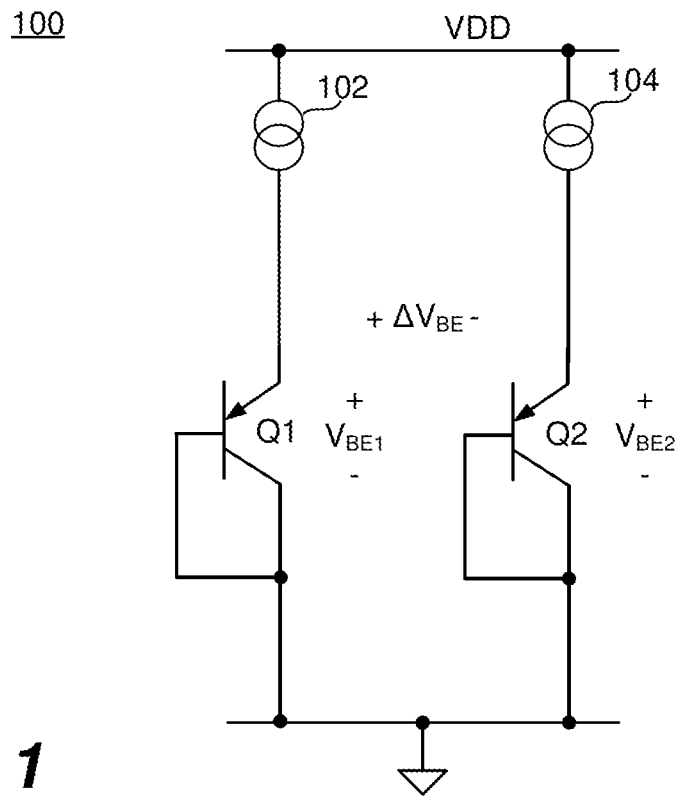
FIG. 1 illustrates an exemplary circuit including to diode connected transistors, which circuit can be used to produce voltage references that are proportional to absolute temperature (PTAT) and complementary (i.e., inverse) to absolute temperature (CTAT).

PTAT voltage references are used commonly for IC temperature sensors and voltage references. Ideally a perfect voltage reference uses a PTAT reference and a CTAT reference to cancel each other to make a voltage that is independent of temperature. A simplified circuit 100, which can be a portion of an IC temperature sensor, is shown in FIG. 1 as including transistors Q1 and Q2, which collectively, can created both types of voltage references (i.e., PTAT and CTAT). More specifically, FIG. 1 shows a circuit 100 that includes an PNP bipolar junction (BJT) transistor Q1 having its base and collector connected together to ground, and having an emitter that is connected to a first current source 102. The circuit 102 also includes a PNP BJT transistor Q2 having its base and collector connected together to ground, and having an emitter that is connected to a second current source 104. As is known in the art, a transistor that has its base and collected connected together is also known as a diode connected transistor, since the transistor functions as a diode. When the current produced by the current source 102 is provided to the diode connected transistor Q1 it produces a first base-to-emitter voltage drop, which can also be referred to as a first forward voltage drop, a first diode voltage drop, a first base-emitter voltage, a first junction voltage, or simply VBE1. Similarly, when the current produced by the current source 104 is provided to the diode connected transistor Q2 it produces a second base-to-emitter voltage drop, which can also be referred to as a second forward voltage drop, a second diode voltage drop, a second base-emitter voltage, a second junction voltage, or simply VBE2. VBE1 and VBE2 are purposely made to be different than one another by configuring the transistors Q1 and Q2 to have different emitter areas and/or different currents, and thus, by causing the transistors Q1 and Q2 to operate at different current densities. For the purpose of this discussion, it is assumed that VBE2>VBE1.

With a constant current it can be shown that the diode voltage drop across the of each PNP transistor, VBE, provides a CTAT voltage temperature relationship. In other words, each of VBE1 and VBE2 is a voltage complementary to absolute temperature, which voltage can also be referred to as VCTAT. The slope of the VCTAT varies in dependence on the supply current and process parameters. A diode voltage drop is also known as a diode voltage, a base-to-emitter voltage drop, a forward voltage drop, a base-emitter voltage, a junction voltage, or simply VBE, as noted above.

The difference between two diode voltages (i.e., between two base-to-emitter voltage drops) forms ΔVBE (delta VBE). In other words, VBE2−VBE1=ΔVBE. It can be shown that this voltage (i.e., ΔVBE) is proportional to absolute temperature (PTAT) and is ideally given by:

$$\Delta V_{BE} = \frac{kT}{q}\ln(n)$$

where k is the Boltzman Constant, T is the absolute temperature, q is the electron charge and n is the constant ratio of the collector currents through the transistors.

Figure 2:
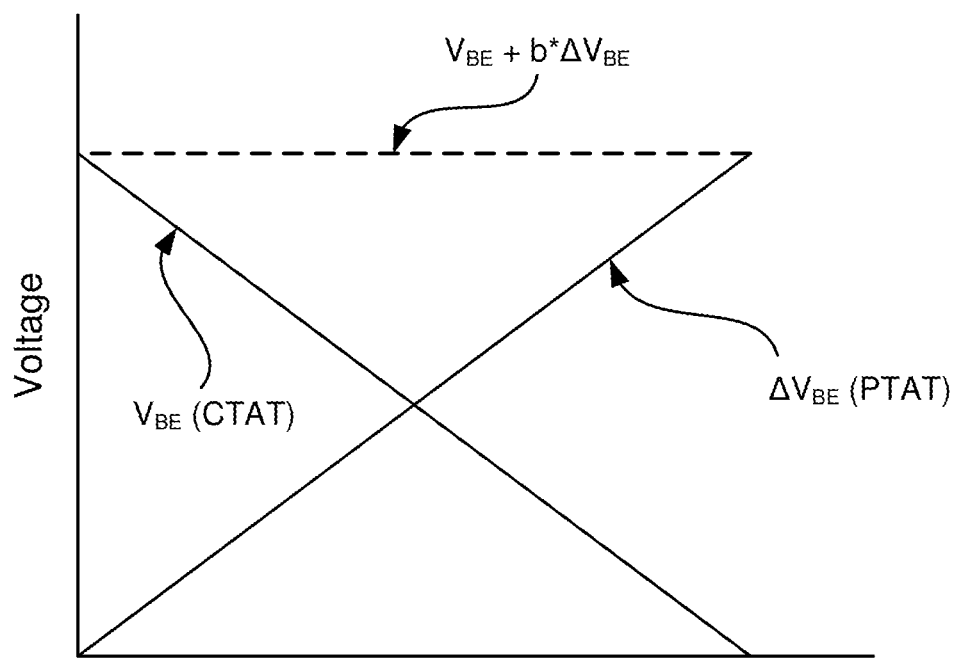
FIG. 2 is an exemplary graph that illustrates the relationship between the two base-to-emitter voltages as a function of temperature.

The relationship between the two base-to-emitter voltage drops (i.e., ΔVBE) as a function of temperature is shown in FIG. 2. Since ΔVBE is a voltage proportional to absolute temperature, ΔVBE can also be referred to as VPTAT, and is shown as an upwardly sloping line in FIG. 2. Similarly, since VBE1 (as well VBE2) is a voltage complementary to absolute temperature, each can be referred to as VCTAT, as noted above. In FIG. 2, the line labeled VBE, which slopes downward, represents one of VBE1 or VBE2. For the purpose of this discussion, it is assumed that the VBE in FIG. 2 is VBE2. Still referring to FIG. 2, if circuit parameters are adjusted (e.g., using a multiplication factor "b") such that the slope of VPTAT is the inverse of VCTAT, one can cancel the effect of the other. This is the basis of bandgap reference voltage supplies.

Figure 3:
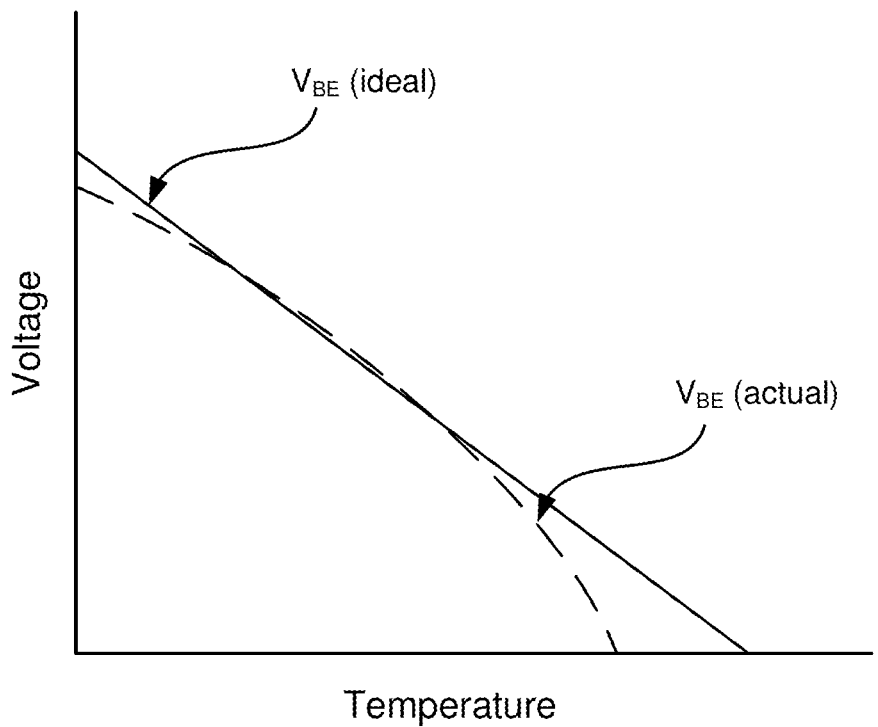
FIG. 3 illustrates how an actual VBE, which is a voltage complementary to absolute temperature (VCTAT) often used in temperature sensors, can vary from an ideal VBE, which can result in significant errors in sensed temperatures.

Due to IC process variations the parameters that may be assumed to be ideal can cause errors in the actual slope and linearity of VCTAT, i.e., VBE1 or VBE2. Errors such as differences in saturation current and current gain between the two diode connected transistors Q1 and Q2 can cause a significant error in ΔVBE of an IC temperature sensor. Referring to FIG. 3, the dashed line therein illustrates that an actual VBE of an IC temperature sensor is typically not perfectly linear (i.e., is typically non-linear). These errors can lead to errors in temperature accuracy.

As will be appreciated from the following discussion, certain embodiments of the present technology utilize single point calibration (i.e., calibration is performed at a single known temperate) to align the actual behavior of a temperature sensor with the desired behavior and reduce the error. By utilizing such embodiments, accuracy within a range of expected temperatures can be improved. The range of expected temperatures can also be referred to herein as the desired temperature range of interest. The desired temperature range can be, e.g., from 36° C. to 40° C., but is not limited thereto.

Figure 4:
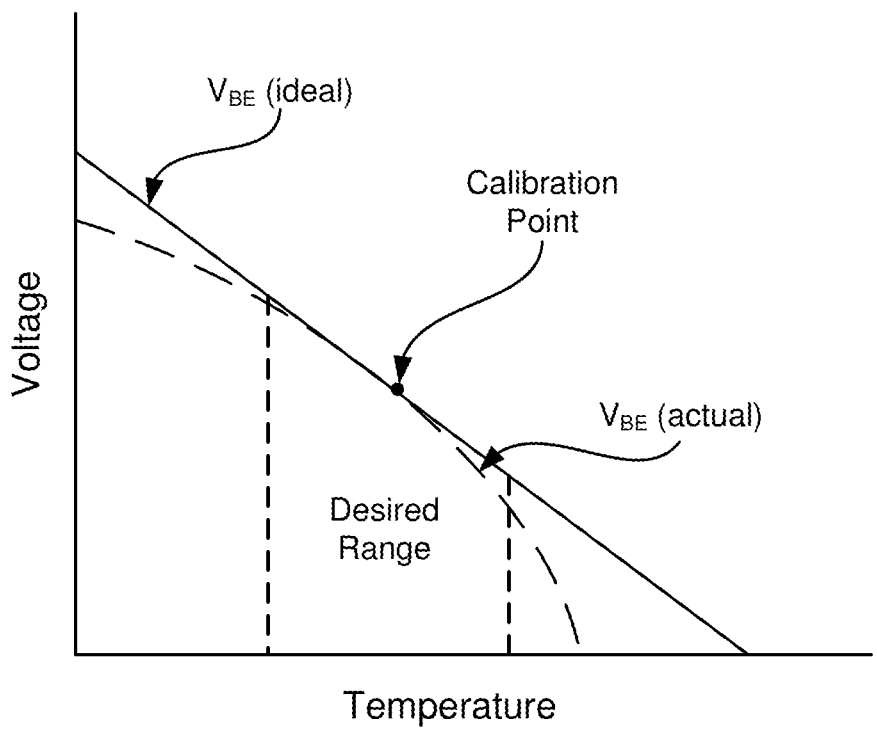
FIG. 4 illustrates that an IC temperature sensor is typically calibrated within a desired temperature range in order to reduce and preferably minimize errors in sensed temperatures.
Figure 5:
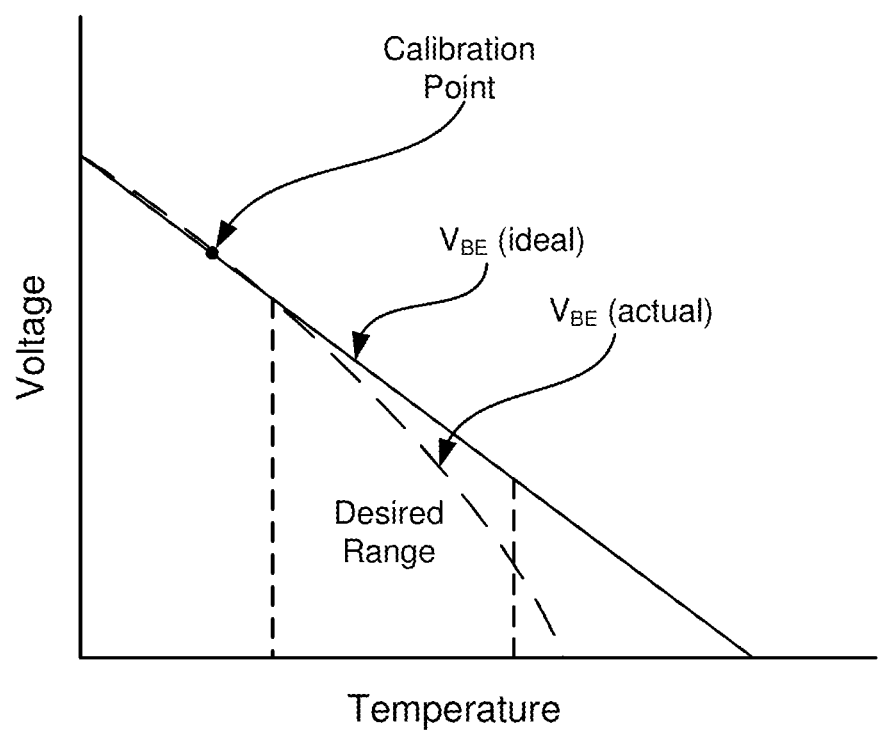
FIG. 5 illustrates that there can be significant errors in sensed temperatures if a conventional IC temperature sensor is calibrated outside a desired temperature range.

Ideally, a conventional IC temperature sensor is calibrated in the mid-range of the desired temperature range of interest, e.g., from 36° C. to 40° C. This is shown for example in FIG. 4. This is a traditional approach to temperature calibration. If the calibration is not within the desired temperature range (e.g., from 36° C. to 40° C.), then significant error can exist depending on the actual VBE. An example is shown in FIG. 5, where the calibration is shown as having been performed below the desired temperature range.

Figure 6A:
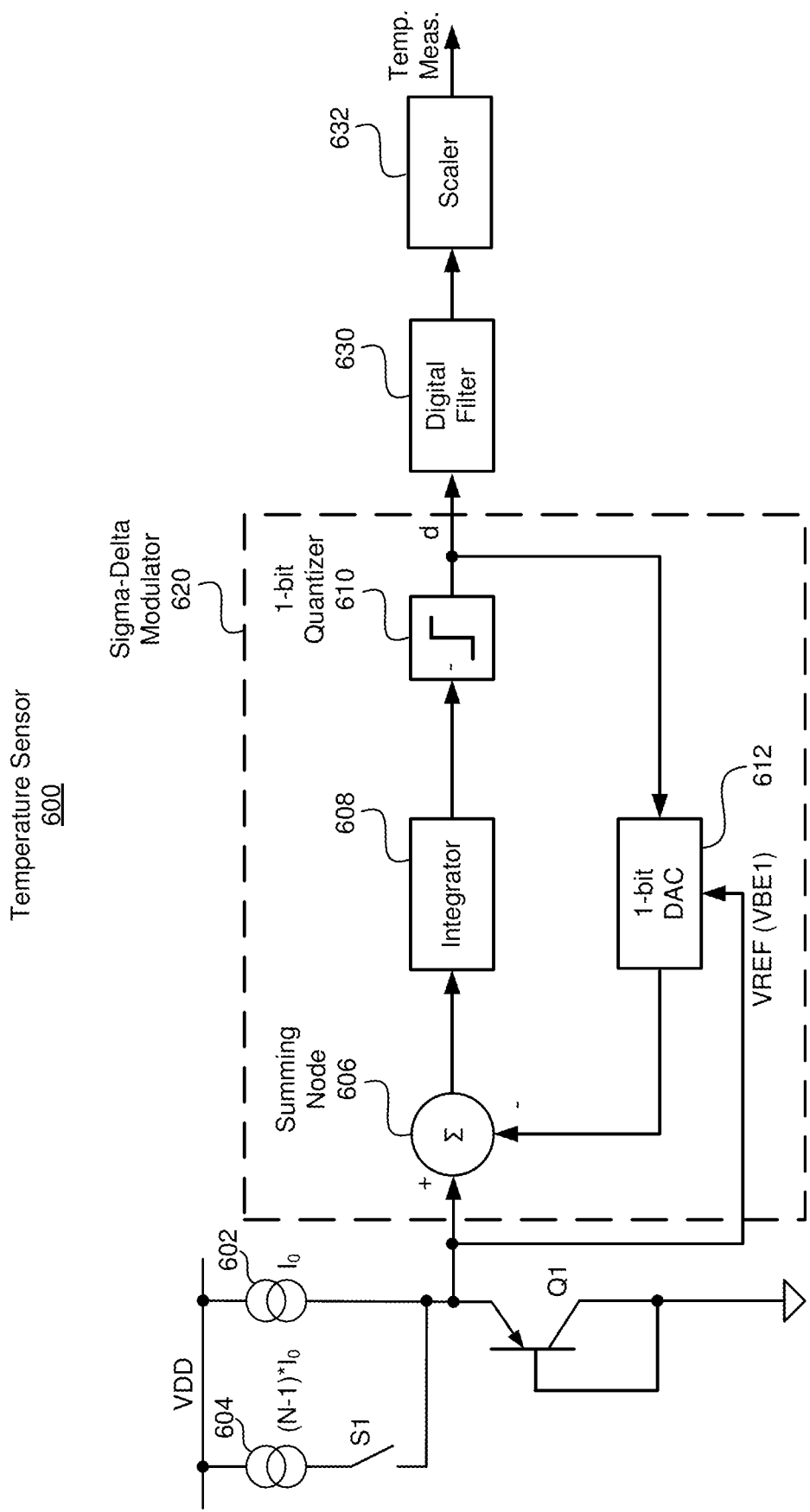
FIG. 6A illustrates a temperature sensor according to an embodiment of the present technology.
Figure 6B:
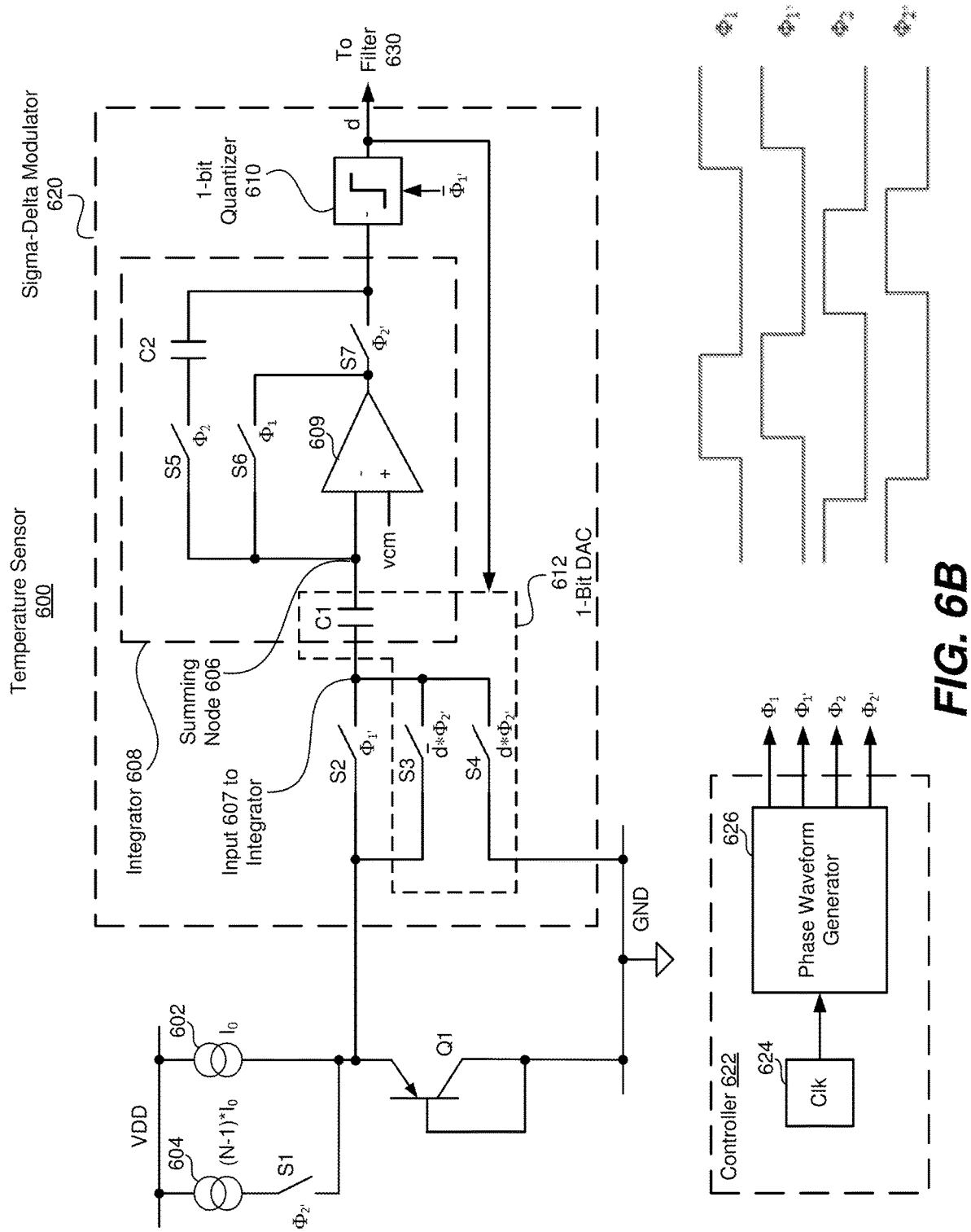
FIG. 6B illustrates additional details of the temperature sensor introduced in FIG. 6A, according to an embodiment of the present technology.

In accordance with certain embodiments of the present technology, a common circuit element (i.e., a common diode device) is used to produce both the VPTAT (i.e., ΔVBE) and the VCTAT (i.e., VBE) that are used for the temperature conversion, as shown in FIGS. 6A and 6B. In such embodiments, VBE1 and VBE2 are created by alternating phases of a current generator, which each phase having a different amplitude. This creates both PTAT and CTAT elements.

The combining of the PTAT and CTAT elements create a 1st order non-linear temperature dependence with output voltage and temperature. By calibrating the temperature at one known value and applying a non-linear correction, an accurate temperature can be determined even if the desired temperature range and the calibration temperature are not close to each other.

Using a common circuit element (i.e., a common diode device) to produce both the VPTAT (i.e., ΔVBE) and the VCTAT (i.e., VBE) has several advantages over a two-element (i.e., two diode device) embodiment. A single holding element (e.g., a single capacitor C1 in FIG. 6B) can be used to produce the VPTAT and the VCTAT, and thus, there is no gain error between the VPTAT and VCTAT. More specifically, by using the same diode connected PNP transistor with different currents, to produce VBE1 and VBE2 (and thus, VBE and ΔVBE, and thus VPTAT and the VCTAT) there is no area mismatch and the ratio of the currents is a fixed (e.g., a given integer) and tightly controlled. Advantageously, any non-linear digital correction that may be needed to achieve a desired accuracy is simple enough that it can be performed by an embedded processor or as a simple lookup table. Further, and importantly, this allows the calibration temperature to be further away from the desired temperature range and remain within the accuracy limits.

Advantageously, embodiments of the present technology allow for a flexible calibration requirement. All that is needed is that an accurate temperature is known at the time of calibration, even if the known accurate temperature is outside the desired temperature range. Beneficially, such a calibration can occur during manufacturing of the IMD including the temperature sensor, prior to implant surgery (of the IMD including the temperature sensor), during implant surgery, or during a follow-up after implant surgery. Further, embodiments of the present technology provide for a simple calibration procedure, where only one temperature reading needs to be taken. Additionally, because such embodiments provide for a low power design, such embodiments do not sacrifice longevity for the sake of a more accurate temperature sensor.

Referring to FIG. 6A, a temperature sensor 600 according to an embodiment of the present technology is shown as including a single diode connected PNP transistor Q1, which depending upon whether a switch S1 is opened or closed, has a current $I_0$ or a current $N*I_0$ provided to its collector. More specifically, in FIG. 6A a current source 602 is shown as being used to produce the current $I_0$, and a current source 604 is shown as being used to produce the current source $(N-1)*I_0$. When the switch S1 is closed, the current $I_0$ plus the current $(N-1)*I_0$, which equals $N*I_0$, is provided to the collector of the diode connected PNP transistor Q1. When the switch S1 is open the current $I_0$ is provided to the collector of the diode connected PNP transistor Q1. Providing the current $N*I_0$ to the collector of the diode connected PNP transistor Q1 produces VBE2; and providing the current $I_0$ to the collector of the diode connected PNP transistor Q1 produces VBE1. One of VBE1 and VBE2 (e.g., VBE1) can be used as the VCTAT. The VPTAT can be generated by determining VBE2−VBE1=ΔVBE. Rather than using the two current sources 602 and 604 to produce VBE1 and VBE2 (and thus, also ΔVBE), N substantially identical current sources (each of which produces the current $I_0$+/−10%) can be used, with all N current sources providing currents to the collector of the diode connected PNP transistor Q1 to produce VBE2, and with one of the N current sources providing a current to the collector of the diode connected PNP transistor Q1 to produce VBE1. In other words, all of the N of the current sources can be active or used to produce VBE2, and one of the N current sources can be active or used to produce VBE1. In such an embodiment, the one of the N current sources that is active or used to produce VBE1 can be changed over time in a round-robin, random, or pseudo-random manner in order to average out any minor mismatches between the N current sources.

The diode connected transistor Q1 is an example of a diode device that can be used to produce a VBE1 and a VBE2, depending whether a first amount of current or a second amount of current is provided to the diode device. In accordance with certain embodiments, VBE1 and VBE2 are produced by alternating between providing the first amount of current and the second amount of current to the same diode device. In certain embodiments, this is achieved using a group of N current sources, where N is ≥3, and each of the N current sources produces a corresponding current that is substantially equal to (within +/−10%) of the currents produced by the other current sources within the group.

Still referring to FIG. 6A, the temperature sensor 600 is also shown as including a summing node 606, an integrator 608, a 1-bit quantizer 610, and a feedback loop including a 1-bit DAC 612. The 1-bit DAC 612 is provided with a reference voltage VREF, which in accordance with certain embodiments of the present technology is VBE1. The summing node 606, the integrator 608, the 1-bit quantizer 610, and the feedback loop including the 1-bit DAC 612 make up a sigma-delta modulator 620. Thus, it can be said that the architecture of the temperature sensor 600 is based on a sigma-delta modulator, which is configured to sense a difference in junction voltage (ΔVBE) for two different current densities using the same diode connected PNP transistor Q1. Additionally, the temperature sensor 600 is configured to use one of the junction voltages (e.g., VBE1) for the feedback. This approach is preferred compared to the approach (e.g., discussed above with reference to FIG. 1) where separate reference voltages that are used for feedback have to be trimmed very accurately. In the embodiment shown in FIG. 6A and described in more detail below with reference to FIG. 6B, the sigma-delta modulator 620 is a first order sigma-delta modulator. However, in alternative embodiments of the present technology, the sigma-delta modulator can be of a higher order (e.g., second order, or third order) for better noise shaping. In accordance with certain embodiments of the present technology, a ratio between the ΔVBE input voltage and the VBE feedback voltage is set to unity by using a same capacitor (e.g., C1 in FIG. 6B) to avoid any analog gain errors, as discussed below in more detail below with reference to FIG. 6B. The digital filter 630 filters the output of the sigma-delta modulator 620 (and more specifically, the output of the 1-bit quantizer 610) to produce a digital value that is indicative of absolute temperature (PTAT). The scaler 632 scales the digital value output by the digital filter 630 and outputs a temperature measurement. In certain embodiments, the temperature measurement that is output by the scaler 632 is corrected for non-linearities using a non-linear equation or a look up table, or the like. Such corrections for non-linearities can be performed, e.g., using firmware or software of the implantable medical device, or using firmware or software of a non-implanted external device (e.g., an external programmer) to which the temperature measurement is uploaded, but is not limited thereto.

Additional details of the temperature sensor 600, initially introduced in FIG. 6A, will now be described with reference to FIG. 6B. Referring to FIG. 6B, the integrator 608 is shown as including a capacitor C1, an operational amplifier (op-amp) 609, a capacitor C2, and switches S5, S6, and S7. The op-amp 609 is connected as an inverting comparator. More specifically, the op-amp 609 includes an inverting (−) input coupled to a terminal of the capacitor C1, a non-inventing (+) input that receives a common mode voltage (vcm) (which can also be referred to as a comparator reference voltage), and an output that is connected to a terminal of the switch S7. The other terminal of the switch S7 is coupled to the 1-bit quantizer 610, and to a terminal of the capacitor C2. The switch S6 is coupled between the output of the op-amp 609 and the inverting (−) input of the op-amp 609. The switch S5 is coupled between a terminal of the capacitor C2 and the inverting (−) input of the op-amp 609. Since the capacitor C2 is solely part of the integrator 608, it can also be referred to as the integrator capacitor C2, or more succinctly as the integrator cap C2.

The inverting (−) input of the op-amp 609 provides the summing node 606. Thus, it can also be said that the switch S6 is coupled between the output of the op-amp 609 and the summing node 606, and the switch S5 is coupled between a terminal of the capacitor C2 and the summing node 606.

The output of the 1-bit quantizer 610, which is labeled "d", has a value of 0 or 1 at any given time, and as shown in FIG. 6B, is used to control the switches S3 and S4 of the 1-bit DAC 612.

The 1-bit DAC 612 is shown as including the switches S3 and S4, as well as the capacitor C1. Accordingly, in the embodiment shown the capacitor C1 is both part of the 1-bit DAC as well as part of the integrator 608. This is advantageous as it ensures that analog gain errors that would otherwise occur (if more than one capacitor were used) are avoided.

FIG. 6B also shows four waveforms, labeled Φ1, Φ1', Φ2, and Φ2', which are used to control the switches S1 through S7. Such waveforms can be generated by a phase waveform generator 626 that receives a clock signal from a clock circuit 624, as shown in FIG. 6B, and generates the waveforms based on the clock signal. More generally, a controller 622 of the temperature sensor 600 can control the switches within the temperature sensor 600. As shown in FIG. 6C, the Φ1 and the Φ2 waveforms are non-overlap phases of the clock, and Φ1' and Φ2' are delayed versions, respectively, of the Φ1 and the Φ2 waveforms. Each of the labels Φ1, Φ1', Φ2, and Φ2' can be used to refer to a respective one of the waveforms, as well as phases during which specific ones of the switches S1 through S6 are closed. For example, showing the label Φ1 next to the switch S6 indicates that the switch S6 is closed whenever the phase waveform Φ1 is high. Another way of saying this is that the switch S6 is closed during Φ1. Where a line is drawn over a label (e.g., where a line is drawn over Φ1), that label can be referred to as the "label" bar (e.g., Φ1 bar), and is the inverse of that phase level. In other words, while Φ1 is high, Φ1 bar is low; and while Φ1 is low, Φ1 bar is high. Similarly, when the value "d" is high, the value "d bar" is low; and when the value "d" is low, the value "d bar" is high, where "d" is the output of the 1-bit quantizer 610.

For the purpose of this discussion, "phase one" is said to occur whenever at least one of Φ1 and is Φ1' are high, and "phase two" is said to occur whenever at least one of Φ2 and is Φ2' are high. Phase one and phase two occur in an alternating fashion at a rate depending upon the clock signal produced by the clock 624. In other words, phases one and two occur in an interleaved manner. The slight delay or offset between the Φ1' and Φ1 signals ensures that switches that are closed during phase one are closed in the appropriate order, e.g., that S6 is closed prior to switches S2. Similarly, the slight delay between the Φ2' and Φ2 signals ensures that switches that are closed during phase two are closed in the appropriate order, e.g., that S5 is closed prior to switches S1 and S7 and one of switches S3 or S4.

During phase one, the switch S1 is open, causing the current $I_0$ to be provided to the collector of the diode-connected transistor Q1, in response to which VBE1 (i.e., a VCTAT) is produced. Additionally, during phase one, the switches S2 and S6 are closed, causing the VBE1 value (i.e., a VCTAT) to be stored on the capacitor C1. In summary, during phase one, the switches S2 and S6 are closed, causing the capacitor C1 to store the VBE1 value (i.e., a VCTAT) that is produced when the current provided to the PN junction of the transistor Q1 is $I_0$. Additionally, during phase one the integrator op-amp 609 is auto-zeroed to minimize its input referred offset. The switches S3, S4, S5 and S7 are open during phase one.

During phase two, the switch S1 is closed, causing the current $N*I_0$ to be provided to the collector of the diode-connected transistor Q1, in response to which VBE2 (i.e., a VCTAT) is produced. Also, during phase two, one of the switches S3 or S4 is closed (depending upon the value of d), the switch S5 is closed, the switch S7 is closed, and the switches S2 and S6 are open. Which one of the switches S3 or S4 is closed depends on the value of "d" output by the 1-bit quantizer 610. During phase two, if d=0, then the switch S3 is closed and the capacitor C1 is connected by the switch S3 to the VBE2 value (producing when the current into the PN junction of the transistor Q1 is $I_0$); or if d=1, then the switch S4 is closed and the capacitor C1 is connected by the switch S4 to ground (GND). Because the switch S5 is closed, the charge on the capacitor C1 is transferred to the integrator cap C2.

When d=1, the charge transfer to the integrator cap C2 is C1*(VBE2−VBE1), i.e., C1*ΔVBE. When d=1, the charge transfer to the integrator cap C2 is −C1*VBE1 (the same formula, but VBE2 is replaced by ground). Accordingly, when d=1, charge is being subtracted from the integrator cap C2.

Over time, the above charges have to balance out, i.e., equal one another. Beneficially, because the same capacitor C1 is used to store VBE1 (which is a VCTAT) as well as ΔVBE (which is VPTAT), the there is no gain error between the VPTAT and VCTAT, and C1 can be removed from both sides of an equation that corresponds to a charge equilibrium. Explain another way, during the first phase, the capacitor C1 is connected between a PN junction node and the input 607 to the integrator 608, which is in reset (the input is at the virtual ground level vcm), so the capacitor C1 samples the value VBE1. During the second phase, the capacitor C1 is connected either to the PN junction node, that will have now the VBE2 level, or to ground, which is 0 volts. So depending on the data bit "d", the capacitor C1 transfers an electric charge at the input 607 to the integrator 608 that can be either C1*(VBE2−VBE1) or −C1*VBE1. Accordingly, the same capacitor C1 is used to either add something proportional to ΔVBE (which is equal to VBE2−VBE1) or to subtract something proportional to VBE1, and the proportionality constant in those two ways is exactly the same value C1. More specifically, the charge equilibrium equation at the input 607 of the integrator 608 can be expressed as follows:

$$(1-dc)*\Delta VBE - dc*\Delta VBE = 0$$

or $$dc*\Delta VBE = (1-dc)*\Delta VBE,$$

where dc is the duty factor (also referred to interchangeably as the duty cycle) at the output of the sigma-delta modulator 620 (which can also be referred to as an analog to digital converter (ADC)), and it is independent of the exact value of the capacitor C1, VBE is VBE1, and ΔVBE=VBE2−VBE1.

The duty cycle (dc) at the output of the sigma-delta modulator 620 is indicative of absolute temperature. However, the dependence on the absolute temperature is somewhat more complicated and can be expressed using the following equation:

$$dc = \Delta VBE/(VBE + \Delta VBE).$$

In order to use the temperature sensor 600 to produce accurate temperature readings, calibration and digital correction should be performed. Such digital correction may be non-linear. The digital calibration and correction can be done in a dedicated digital signal processor (DSP) or in software or firmware. In certain embodiments, the digital correction can be performed in software, external to the temperature sensor 600, e.g., by an external programmer or some other external device (e.g., 902 in FIG. 9), or more generally, by a sub-system external to the temperature sensor 600, which would be useful since computation resources of the temperature sensor 600 and/or IMD (e.g., 910 in FIG. 9) may be limited. The VBE and ΔVBE terms can be combined to determine a constant bandgap voltage (VBG) as follow:

$$V_{BG} = V_{BE} + (b+1) \cdot \Delta V_{BE}$$

where b is a parameter (e.g., of about 10.0) and it is slightly dependent on the process corner for the PN junction of the transistor Q1.

Then, the variation of the PN junction voltage drop ΔVBE, which is proportional to absolute temperature (PTAT), can be written as follows:

$$\Delta V_{BE} = V_{BG} \cdot \frac{d}{1 + b \cdot d}$$

If the parameter b is chosen such that the bandgap voltage (VBG) has a zero temperature coefficient (tempco), the previous relation implies that the absolute temperature can be found from the following equation:

$$T \propto \frac{d}{1 + b \cdot d}$$

The proportionality constant can be determined by calibration at a known (room) temperature. Let $d_0$ be the modulator output at the know temperature $T_0$. Then the absolute temperature can be determined by the following equation:

$$T = T_0 \cdot \frac{1 + b \cdot d_0}{d_0} \cdot \frac{d}{1 + b \cdot d} = T_0 + \frac{T_0}{d_0} \cdot \frac{d - d_0}{1 + b \cdot d}$$

It is preferable to have programmable parameters for the offset to the absolute temperature and the process parameter b, that should be computed from a look up table based on the modulator output $d_0$ at the known temperature $T_0$.

Figure 7:
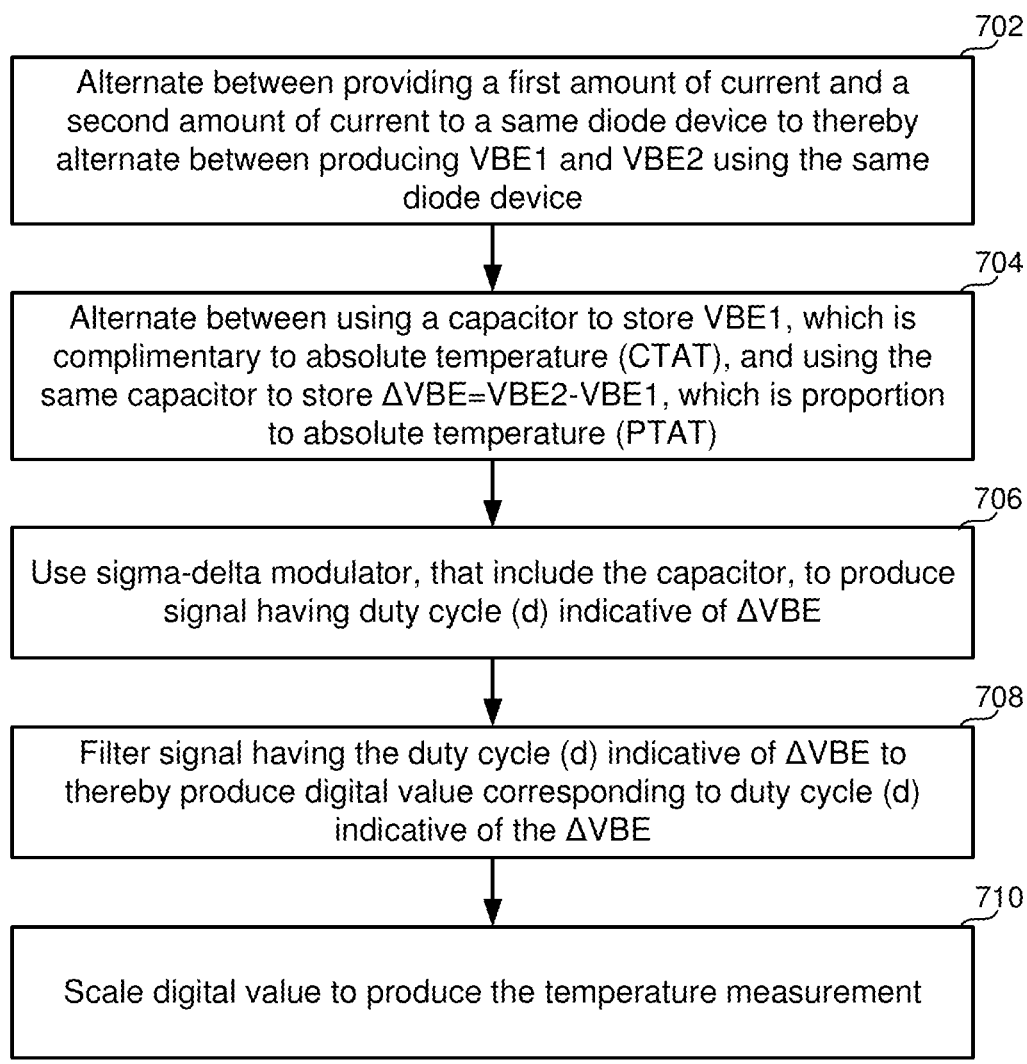
FIG. 7 is a high level flow diagram that is used to summarize methods according to certain embodiments of the present technology.

The high level flow diagram of FIG. 7 will now be used to summarize methods according to certain embodiments of the present technology. Referring to FIG. 7, step 702 involves alternating between providing a first amount of current and a second amount of current to a same diode device to thereby alternate between producing a first base-to-emitter voltage drop (VBE1) and a second base-to-emitter voltage drop (VBE2) using the same diode device. Referring back to FIGS. 6A and 6B, the diode connected transistor Q1 can be used as the diode device, and the current sources 602 and 604 and the switch S1 can be used to alternate between providing the first amount of current and the second amount of current to the same diode device to thereby alternate between producing VBE1 and VBE2 using the same diode device. As explain above, additional current sources and switches can alternatively be used.

Referring again to FIG. 7, step 704 involves alternating between using a capacitor to store the VBE1, which is complimentary to absolute temperature (CTAT), and using the same capacitor to store a ΔVBE=VBE2−VBE1, which is proportion to absolute temperature (PTAT). Referring back to FIG. 6B, the capacitor C1 can be used to perform step 704.

Referring again to FIG. 7, step 706 involves using a sigma-delta modulator, which includes the same capacitor (e.g., C1 in FIG. 6B) to produce a signal having a duty cycle (dc) indicative of ΔVBE. Referring back to FIG. 6B, the sigma-delta modulator 620 can be used to perform step 706.

Referring again to FIG. 7, step 708 involves filtering the signal having the duty cycle (dc) indicative of the ΔVBE to thereby produce a digital value corresponding to the duty cycle (dc) indicative of the ΔVBE, which as noted above, is proportion to absolute temperature (PTAT). Referring back to FIG. 6A, the digital filter 630 can be used to perform step 708.

Referring again to FIG. 7, step 710 involves scaling the digital value, produced at step 708, to thereby produce a temperature measurement. In accordance with certain embodiments, the temperature measurement produced at step 710 is within +/−0.1° C. of an actual temperature. Referring briefly back to FIG. 6A, step 710 can be performing using the scaler 632. The scaler 632 can be implemented, e.g., using a processor that uses an equation to calculate a temperature based on the digital value output by the digital filter 630, or using a processor that uses a lookup table (LUT) to look up a temperature based on the digital value output by the digital filter 630. Other variations are also possible and within the scope of the embodiments described herein. Step 710, or a further step that follows step 710, can involve performing a digital correction to compensate for non-linearities in analog to digital conversions performed by the sigma-delta modulator 620. Such a digital correction can be performed using a non-linear equation or a look up table, but is not limited thereto. The digital correction can be performed, e.g., in firmware or software implemented by the IMD (e.g., 902 in FIG. 9) that implements the method of FIG. 7, or in firmware or software implemented by an external device (e.g., 902 in FIG. 9) to which a non-corrected temperature measurement is uploaded.

Figure 8:
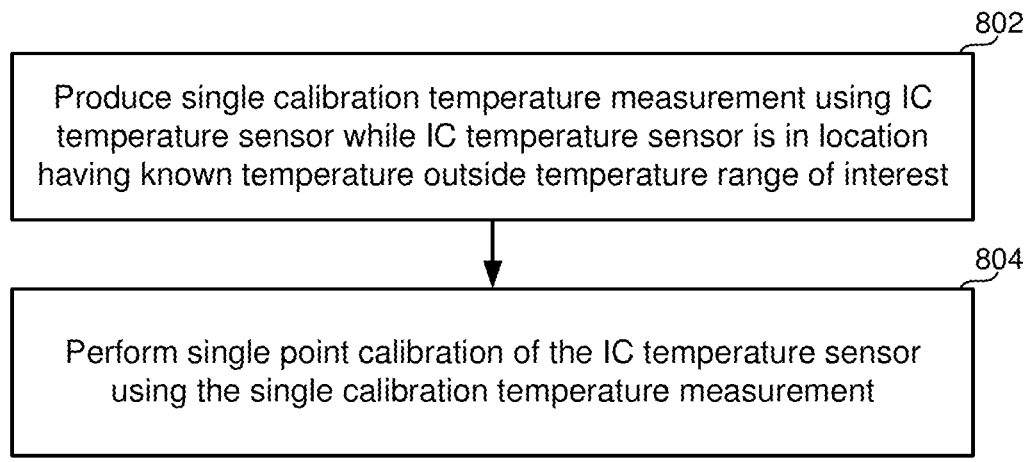
FIG. 8 is a high level flow diagram that is used to summarize a method for performing a single point calibration according to certain embodiments of the present technology.

FIG. 8 is a high level flow diagram that will now be used to summarize a method for performing a single point calibration according to certain embodiments of the present technology wherein the diode device (e.g., the diode connected transistor Q1) and the capacitor (e.g., C1) are components of an integrated circuit (IC) temperature sensor. Referring to FIG. 8, step 802 involves producing a single calibration temperature measurement using the IC temperature sensor while the IC temperature sensor is in a location having a known temperature. Step 804 involves performing a single point calibration of the IC temperature sensor using the single calibration temperature measurement. In accordance with certain embodiments, the IC temperature sensor is for use within a specified temperature range of interest, e.g., from about 36° C. to about 40° C. Beneficially, the single point calibration can be performed outside the specified temperature range of interest, and thus, the single calibration temperature measurement used for the single point calibration can be outside the specified temperature range of interest while still achieving an accuracy of +/−0.1° C. of an actual temperature. For an example, the single point calibration can be performed at room temperature (e.g., 21° C.) during manufacturing, yet the temperature sensor can still be accurate to at least +/−0.1° C. within the range of interest, e.g., a range of body temperatures from approximately 36° C. to 40° C.

An exemplary IMD that can include the temperature sensor 600 discussed above with reference to FIGS. 6A and 6B, and that can be used to perform the methods summarized with reference to FIGS. 7 and 8, will now be discussed below with reference to FIGS. 9A and 9B.

Exemplary IMD

Figure 9A:
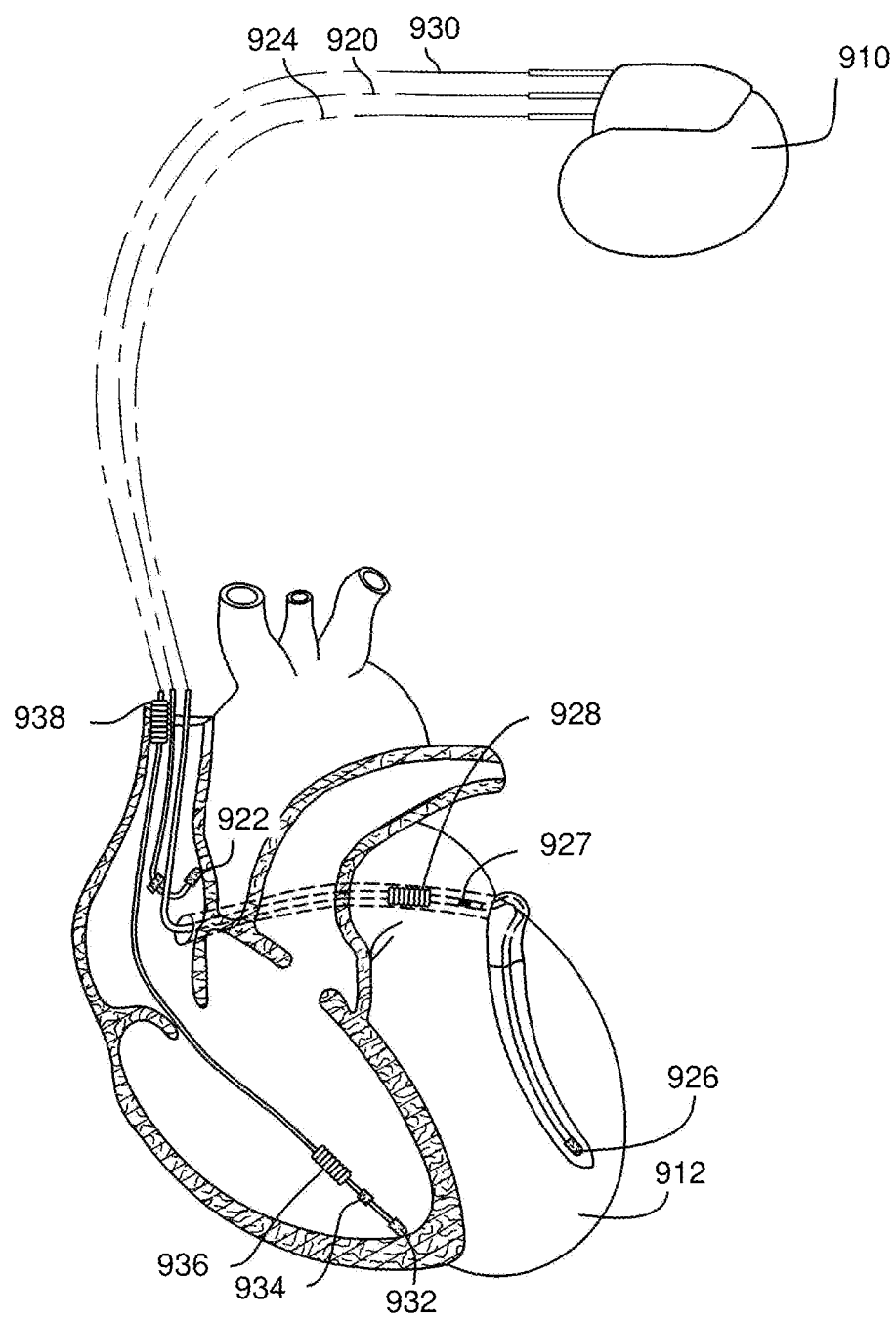
FIG. 9A is an exemplary implantable medical device (IMD) within which embodiments of the present technology may be implemented.

Referring to FIG. 9A, an exemplary IMD 910 (also referred to as a pacing device, a pacing apparatus, a stimulation device, an implantable device or simply a device) is in electrical communication with a patient's heart 912 by way of three leads, 920, 924 and 930, suitable for delivering multi-chamber stimulation. While not necessary to perform embodiments of the present technology, the exemplary IMD 910 can also be capable of delivering shock therapy.

To sense atrial cardiac signals and to provide right atrial chamber stimulation therapy, the IMD 910 is coupled to an implantable right atrial lead 920 having at least an atrial tip electrode 922, which typically is implanted in the patient's right atrial appendage. To sense left atrial and ventricular cardiac signals and to provide left-chamber pacing therapy, the IMD 910 is coupled to a "coronary sinus" lead 924 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 924 is designed to receive left atrial and ventricular cardiac signals and to deliver left atrial and ventricular pacing therapy using at least a left ventricular tip electrode 926, left atrial pacing therapy using at least a left atrial ring electrode 927, and shocking therapy using at least a left atrial coil electrode 928. The present technology may of course be practiced with a coronary sinus lead that does not include left atrial sensing, pacing or shocking electrodes.

The IMD 910 is also shown in electrical communication with the patient's heart 912 by way of an implantable right ventricular lead 930 having, in this embodiment, a right ventricular tip electrode 932, a right ventricular ring electrode 934, a right ventricular (RV) coil electrode 936, and an SVC coil electrode 938. Typically, the right ventricular lead 930 is transvenously inserted into the heart 912 so as to place the right ventricular tip electrode 932 in the right ventricular apex so that the RV coil electrode 936 will be positioned in the right ventricle and the SVC coil electrode 938 will be positioned in the superior vena cava. Accordingly, the right ventricular lead 930 is capable of receiving cardiac signals and delivering stimulation in the form of pacing and shock therapy to the right ventricle. It will be understood by those skilled in the art that other lead and electrode configurations such as epicardial leads and electrodes may be used in practicing the technology. For example, only a single lead, or only two leads, may be connected to the IMD. It should also be understood that the IMD can alternatively be a leadless device, such as an implantable monitor and/or a leadless pacer.

Figure 9B:
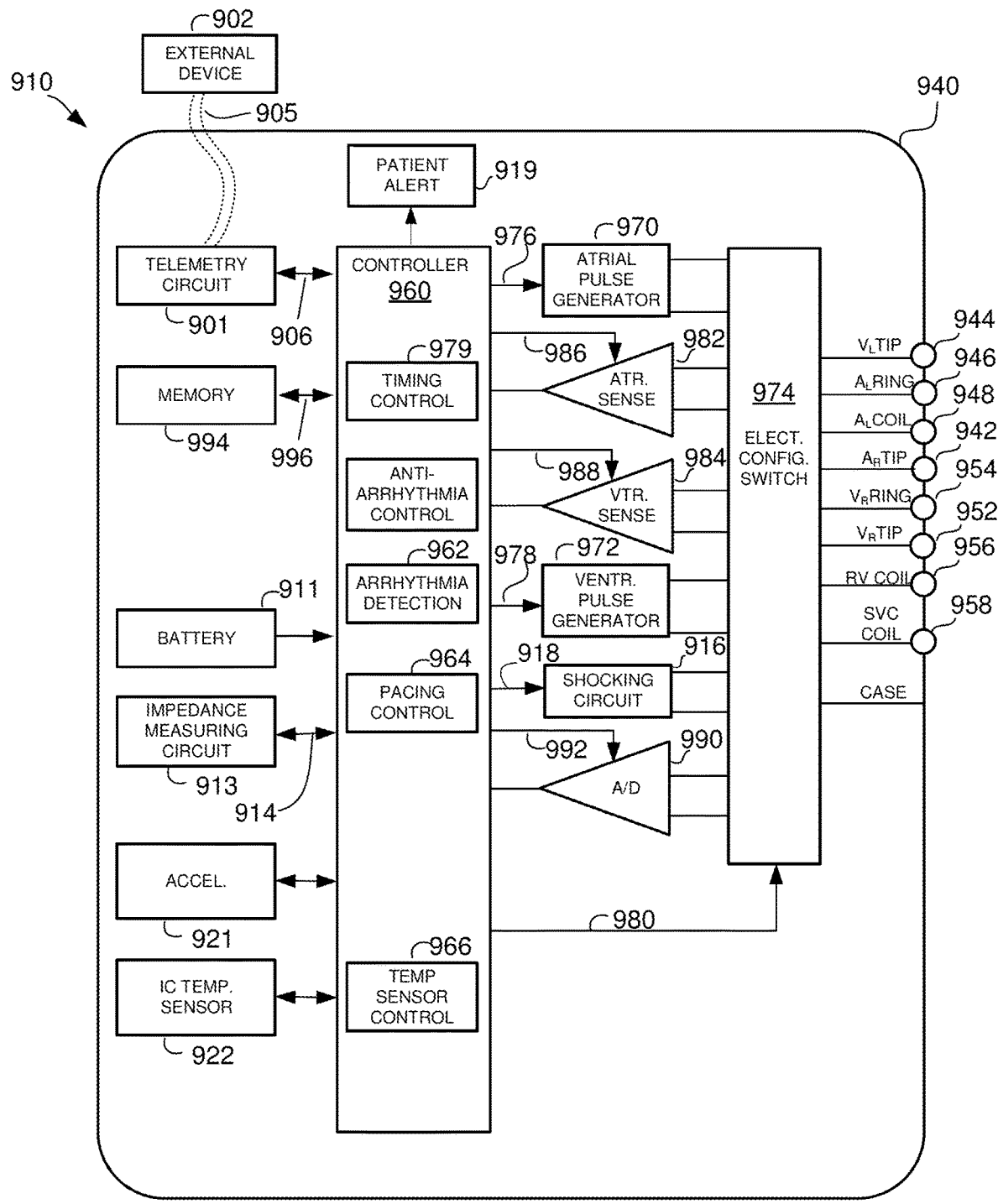
FIG. 9B is a simplified block diagram that is used to describe additional details of the IMD introduced in FIG. 9A.

As illustrated in FIG. 9B, a simplified block diagram is shown of the multi-chamber implantable device 910, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 940 for the IMD 910, shown schematically in FIG. 9B, is often referred to as the "can", "case" or "case electrode" and may be programmable to electrically act as the return electrode for all "unipolar" modes. The housing 940 may further be used as a return electrode alone or in combination with one or more of the coil electrodes, 928, 936 and 938, for shocking purposes. The housing 940 further includes a connector (not shown) having a plurality of terminals, 942, 944, 946, 948, 952, 954, 956, and 958 (shown schematically and, for convenience, the names of the electrodes to which they are connected are shown next to the terminals). As such, to achieve right atrial sensing and pacing, the connector includes at least a right atrial tip terminal (AR TIP) 942 adapted for connection to the atrial tip electrode 922.

To achieve left atrial and ventricular sensing, pacing and shocking, the connector includes at least a left ventricular tip terminal (VL TIP) 944, a left atrial ring terminal (AL RING) 946, and a left atrial shocking terminal (AL COIL) 948, which are adapted for connection to the left ventricular ring electrode 926, the left atrial tip electrode 927, and the left atrial coil electrode 928, respectively.

To support right ventricle sensing, pacing and shocking, the connector further includes a right ventricular tip terminal (VR TIP) 952, a right ventricular ring terminal (VR RING) 954, a right ventricular shocking terminal (RV COIL) 956, and an SVC shocking terminal (SVC COIL) 958, which are adapted for connection to the right ventricular tip electrode 932, right ventricular ring electrode 934, the RV coil electrode 936, and the SVC coil electrode 938, respectively.

At the core of the IMD 910 is a programmable microcontroller 960 which controls the various types and modes of stimulation therapy. As is well known in the art, the microcontroller 960 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 960 includes the ability to process or monitor input signals (data) as controlled by a program code stored in a designated block of memory. The details of the design of the microcontroller 960 are not critical to the present technology. Rather, any suitable microcontroller 960 can be used to carry out the functions described herein. The use of microprocessor-based control circuits for performing timing and data analysis functions are well known in the art. In specific embodiments of the present technology, the microcontroller 960 performs some or all of the steps associated with arrhythmia detection. The microcontroller 960 can be used to implement that controller 622 discussed above with reference to FIG. 6B.

Representative types of control circuitry that may be used with the technology include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 970 and a ventricular pulse generator 972 generate pacing stimulation pulses for delivery by the right atrial lead 920, the right ventricular lead 930, and/or the coronary sinus lead 924 via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators, or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry 979 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, etc.) by selectively closing the appropriate combination of switches (not shown) as is known in the art.

Atrial sensing circuits 982 and ventricular sensing circuits 984 may also be selectively coupled to the right atrial lead 920, coronary sinus lead 924, and the right ventricular lead 930, through the switch 974 for detecting the presence of cardiac activity in each of the four chambers of the heart. Accordingly, the atrial (ATR. SENSE) and ventricular (VTR. SENSE) sensing circuits, 982 and 984, may include dedicated sense amplifiers, multiplexed amplifiers, or shared amplifiers. The switch 974 determines the "sensing polarity" of the cardiac signal by selectively closing the appropriate switches, as is also known in the art. In this way, the clinician may program the sensing polarity independent of the stimulation polarity.

Each sensing circuit, 982 and 984, preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 910 to deal effectively with the difficult problem of sensing the low amplitude signal characteristics of atrial or ventricular fibrillation.

The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity, in the appropriate chambers of the heart. The sensing circuits, 982 and 984, in turn, receive control signals over signal lines, 986 and 988, from the microcontroller 960 for purposes of measuring cardiac performance at appropriate times, and for controlling the gain, threshold, polarization charge removal circuitry (not shown), and timing of any blocking circuitry (not shown) coupled to the inputs of the sensing circuits, 982 and 986. The sensing circuits can be used, for example, to acquire IEGM signals.

For arrhythmia detection, the IMD 910 includes an arrhythmia detector 962 that utilizes the atrial and ventricular sensing circuits, 982 and 984, to sense cardiac signals to determine whether a rhythm is physiologic or pathologic. The timing intervals between sensed events (e.g., P-waves, R-waves, and depolarization signals associated with fibrillation) are then classified by the microcontroller 960 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 962 can be implemented within the microcontroller 960, as shown in FIG. 9B. Thus, this detector 962 can be implemented by software, firmware, or combinations thereof. It is also possible that all, or portions, of the arrhythmia detector 962 can be implemented using hardware. Further, it is also possible that all, or portions, of the arrhythmia detector 962 can be implemented separate from the microcontroller 960.

The stimulation device 910 is also shown as including a pacing controller 964, which can adjust a pacing rate and/or pacing intervals. The pacing controller 964 can be implemented within the microcontroller 960, as shown in FIG. 9B. Thus, the pacing controller 964 can be implemented by software, firmware, or combinations thereof. It is also possible that all, or portions, of the pacing controller 964 can be implemented using hardware.

The accelerometer 921 of the IMD 910 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables (e.g., acceleration, and/or vibration), but is not limited thereto. Depending upon implementation, the accelerometer 921 can be used to detect posture and/or motion of a patient in which an IMD 910 including the accelerometer 921 is implanted.

Additionally, the IMD 910 is shown as including a temperature sensor control 966. In accordance with certain embodiments of the present technology, the temperature sensor control 966 can be used control the various switches shown in and discussed above with reference to FIG. 6B. Thus, the temperature sensor control 966 can be implemented by software, firmware, hardware, or combinations thereof. It is also possible that all, or portions, of the temperature sensor control 966 can be implemented using dedicated hardware, such as using an application specific integrated circuit (ASIC). More generally, the temperature sensor control 966 can be implemented by a controller, wherein the controller may be a microcontroller (e.g., 960), or an ASIC, but is not limited thereto.

Still referring to FIG. 9B, cardiac signals and/or other signals can be applied to the inputs of an analog-to-digital (A/D) data acquisition system 990. The data acquisition system 990 is configured to acquire intracardiac electrogram signals, convert the raw analog data into a digital signal, and store the digital signals for later processing and/or telemetric transmission to an external device 902. The data acquisition system 990 is coupled to the right atrial lead 920, the coronary sinus lead 924, and the right ventricular lead 930 through the switch 974 to sample cardiac signals across any pair of desired electrodes.

The data acquisition system 990 can be coupled to the microcontroller 960, or other detection circuitry, for detecting an evoked response from the heart 912 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 960 detects a depolarization signal during a window following a stimulation pulse, the presence of which indicates that capture has occurred. The microcontroller 960 enables capture detection by triggering the ventricular pulse generator 972 to generate a stimulation pulse, starting a capture detection window using the timing control circuitry 979 within the microcontroller 960, and enabling the data acquisition system 990 via control signal 992 to sample the cardiac signal that falls in the capture detection window and, based on the amplitude, determines if capture has occurred. The data acquisition system 990 may also be used to acquire signals produced by the sensors 919 and/or 921, and may convert analog signals produced by such sensor to digital signals. It is also possible that the sensors 919 and/or 921 output digital signals. The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present technology.

The microcontroller 960 is further coupled to the memory 994 by a suitable data/address bus 996, wherein the programmable operating parameters used by the microcontroller 960 are stored and modified, as required, in order to customize the operation of the IMD 910 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 912 within each respective tier of therapy. The memory 994 can also be used to store accurate temperature measurements obtained using a temperature sensor (e.g., 600) of an embodiments of the present technology described herein. The memory 994 can store either uncorrected temperature measurement data or corrected temperature measurement data. Storing uncorrected temperature measurement data would be useful for reducing computational requirements on the temperature sensor 600 and the microcontroller 960, or more generally on the IMD 910, in which case the external device 902 (e.g., an external programmer) can perform the digital corrections.

The operating parameters of the IMD 910 may be non-invasively programmed into the memory 994 through a telemetry circuit 901 in telemetric communication with an external device 902, such as a programmer, transtelephonic transceiver, or a diagnostic system analyzer. The telemetry circuit 901 can be activated by the microcontroller 960 by a control signal 906. The telemetry circuit 901 advantageously allows intracardiac electrograms and status information relating to the operation of the device 910 (as contained in the microcontroller 960 or memory 994) to be sent to the external device 902 through an established communication link 904. The telemetry circuit 901 can also be used to trigger alarms or alerts of the external device 902, or to instruct the external device 902 to notify a caregiver regarding detection of various episodes, occurrences and changes in conditions that are detected using embodiments of the present technology. The telemetry circuity 901 can also be used to transfer from the IMD 910 to the external device 902 temperature measurements obtained using a temperature sensor (e.g., 600) of an embodiments of the present technology described herein.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The IMD 910 additionally includes a battery 911 which provides operating power to all of the circuits shown in FIG. 9B. If the implantable device 910 also employs shocking therapy, the battery 911 should be capable of operating at low current drains for long periods of time, and then be capable of providing high-current pulses (for capacitor charging) when the patient requires a shock pulse. The battery 911 should also have a predictable discharge characteristic so that elective replacement time can be detected.

As further shown in FIG. 9B, the IMD 910 is also shown as having an impedance measuring circuit 913 which is enabled by the microcontroller 960 via a control signal 914. The known uses for an impedance measuring circuit 913 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 913 is advantageously coupled to the switch 974 so that any desired electrode may be used. The impedance measuring circuit 913 is not critical to the present technology and is shown only for completeness.

In the case where the IMD 910 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 960 further controls a shocking circuit 916 by way of a control signal 918. The shocking circuit 916 generates shocking pulses of low (up to 0.5 Joules), moderate (0.5-10 Joules), or high energy (11 to 40 Joules), as controlled by the microcontroller 960. Such shocking pulses are applied to the patient's heart 912 through at least two shocking electrodes, and as shown in this embodiment, selected from the left atrial coil electrode 928, the RV coil electrode 936, and/or the SVC coil electrode 938. As noted above, the housing 940 may act as an active electrode in combination with the RV electrode 936, or as part of a split electrical vector using the SVC coil electrode 938 or the left atrial coil electrode 928 (i.e., using the RV electrode as a common electrode).

The above described IMD 910 was described as an exemplary pacing device. One or ordinary skill in the art would understand that embodiments of the present technology can be used with alternative types of implantable devices. Accordingly, embodiments of the present technology should not be limited to use only with the above described device.

As noted above, embodiments of the present technology may also be used with a leadless pacemaker, or with an implantable cardiac monitor that does not provide any therapy. Exemplary leadless pacemakers are described in U.S. Pat. No. 8,996,109 (Karst et al.) and U.S. Pat. No. 9,533,163 (Klimovitch et al.), which are incorporated herein by reference. An implantable cardiac monitor that does not provide any therapy can, for example, store accurate temperature measurements, and such stored information can be uploaded to an external device for analysis and or display.

Embodiments of the present technology describe above generally pertain to temperature sensors for including in IMDs, and methods for use therewith. Such embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed technology. For example, it would be possible to combine or separate some of the steps shown in FIGS. 7 and 8. For another example, it is possible to change the boundaries of some of the blocks shown in FIGS. 6A and 6B.

It is noted that the term "base on", as used herein, should be interpreted as meaning based at least in part on, unless stated otherwise. In other words, where a decision is based on something, that decision can also be based on additional things. By contrast, where a decision is based solely on something, that decision is not also based on additional things.

The previous description of the preferred embodiments is provided to enable any person skilled in the art to make or use the embodiments of the present technology. While the technology has been particularly shown and described with reference to preferred embodiments thereof, it will be understood by those skilled in the art that various changes in form and details may be made therein without departing from the spirit and scope of the technology.

What is claimed is:

1. A method for producing a temperature measurement for use in an implantable medical device (IMD), the method comprising:
   alternating between providing a first amount of current to a diode device and a second amount of current to the same diode device to thereby alternate between producing a first base-to-emitter voltage drop (VBE1) and a second base-to-emitter voltage drop (VBE2) using the same diode device;
   alternating between using a capacitor to store the VBE1, which is complimentary to absolute temperature (CTAT), and using the same capacitor to store a ΔVBE=VBE2−VBE1, which is proportion to absolute temperature (PTAT);
   producing, using a sigma-delta modulator that includes the same capacitor used to store the VBE1 and the ΔVBE, a signal having a duty cycle (dc) indicative of the ΔVBE; and
   producing a temperature measurement based on the signal having the duty cycle (dc) indicative of the ΔVBE;
   wherein the sigma-delta modulator includes a summing node, an integrator, a 1-bit quantizer, and a 1-bit digital-to-analog converter (DAC), the integrator including an operational amplifier (op-amp) having first and second inputs and an output, with one of the first and second inputs coupled to the summing node, and the integrator also including a switch between the output of the op-amp and an input of the 1-bit quantizer;
   wherein the same capacitor that is used to store both the VBE1 and the ΔVBE is part of both the integrator and the 1-bit DAC of the sigma-delta modulator; and
   wherein the method includes controlling the switch to selectively couple the output of the op-amp to the input of the 1-bit quantizer.

2. The method of claim 1, wherein:
   the summing node is coupled to a terminal of the diode device that alternately produces the VBE1 and the VBE2;
   the signal having the duty cycle (dc) indicative of the ΔVBE is output by the 1-bit quantizer; and
   the VBE1 that is stored on the capacitor is used as a reference voltage for the 1-bit DAC, thereby eliminating a need for a separate reference voltage to be trimmed and used as the reference voltage for the 1-bit DAC.

3. The method of claim 1, wherein the producing the temperature measurement, based on the signal having the duty cycle (dc) indicative of the ΔVBE, comprises:
   filtering the signal having the duty cycle (dc) indicative of the ΔVBE to thereby produce a digital value corresponding to the duty cycle (dc) indicative of the ΔVBE; and
   using at least one of a processor, an equation, or a look up table (LUT), to produce the temperature measurement based on the digital value corresponding to the duty cycle (dc) indicative of the ΔVBE.

4. The method of claim 1, wherein the diode device and the capacitor are components of an integrated circuit (IC) temperature sensor, and wherein the method further comprises:
   producing a single calibration temperature measurement using the IC temperature sensor while the IC temperature sensor is in a location having a known temperature; and
   performing a single point calibration of the IC temperature sensor using the single calibration temperature measurement.

5. The method of claim 4, wherein:
   the IC temperature sensor is for use within a specified temperature range of interest; and
   the known temperature, of the location where the IC temperature sensor is located when the single calibration temperature measurement is produced, is outside the specified temperature range of interest, and thus, the single calibration temperature measurement used for the single point calibration is outside the specified temperature range of interest.

6. The method of claim 1, wherein the temperature measurement is within +/−0.1° C. of an actual temperature.

7. The method of claim 1, wherein the alternating between providing the first amount of current and the second amount of current to the same diode device comprises:
using each current source, of a group of N current sources, to produce a corresponding current that is substantially equal to the currents produced by the other current sources within the group, wherein N is ≥3; and
alternating between connecting one of the N current sources in the group to the diode device to thereby cause the providing of the first amount of current to the diode device, and connecting the N current sources in the group to the diode device to thereby cause the providing of the second amount of current to the diode device;
wherein which one of the N current sources is connected to the diode device, to thereby cause the providing of the first amount of current to the diode device, is changed in a round-robin, random, or pseudo-random manner so that small differences in the currents produced by the N current sources are averaged out over time.

8. The method of claim 1, wherein the producing the signal having the duty cycle (dc) indicative of the ΔVBE includes:
based on an output of the 1-bit quantizer, selectively transferring a voltage equal to either C1*ΔVBE or −C1*VBE1 from the capacitor, which is part of both the integrator and the 1-bit DAC of the sigma-delta modulator, to a further capacitor of the integrator,
where C1 is the value of the capacitor that is part of both the integrator and the 1-bit DAC of the sigma-delta modulator.

9. A temperature sensor for use in an implantable medical device (IMD), the temperature sensor comprising:
a diode device;
a plurality of current sources;
a controller configured to control alternating between providing a first amount of current and a second amount of current produced using the current sources, or subsets thereof, to the diode device, to thereby alternate between producing a first base-to-emitter voltage drop (VBE1) and a second base-to-emitter voltage drop (VBE2) using the same diode device; and
a sigma-delta modulator including a capacitor configured to alternate between storing the VBE1, which is complimentary to absolute temperature (CTAT), and storing a ΔVBE=VBE2−VBE1, which is proportion to absolute temperature (PTAT);
the sigma-delta modulator configured to produce a signal having a duty cycle (dc) indicative of the ΔVBE:
wherein the sigma-delta modulator includes a summing node, an integrator, a 1-bit quantizer, and a 1-bit digital-to-analog converter (DAC), the integrator including an operational amplifier (op-amp) having first and second inputs and an output, with one of the first and second inputs coupled to the summing node, and the integrator also including a switch between the output of the op-amp and an input of the 1-bit quantizer;
wherein the same capacitor that is used to store both the VBE1 and the ΔVBE is part of both the integrator and the 1-bit DAC of the sigma-delta modulator; and
wherein the switch is controlled to selectively couple the output of the op-amp to the input of the 1-bit quantizer.

10. The temperature sensor of claim 9, wherein:
the summing node is coupled to a terminal of the diode device that alternately produces the VBE1 and the VBE2;
the signal having the duty cycle (dc) indicative of the ΔVBE is output by the 1-bit quantizer; and
the VBE1 that is stored on the capacitor is also used as a reference voltage for the 1-bit DAC, thereby eliminating a need for a separate reference voltage to be trimmed and used as the reference voltage for the 1-bit DAC.

11. The temperature sensor of claim 9, wherein the sigma-delta modulator comprises a first order or higher order sigma-delta modulator.

12. The temperature sensor of claim 9, further comprising:
a filter configured to filter the signal having the duty cycle (dc) indicative of the ΔVBE to thereby produce a digital value corresponding to the duty cycle (dc) indicative of the ΔVBE; and
a scaler configured to produce the temperature measurement based on the digital value corresponding to the duty cycle (dc) indicative of the ΔVBE;
wherein a digital correction can be applied to the temperature measurement produced by the scaler, with the digital correction performed by the temperature sensor, by the IMD, or by an external device to which the temperature measurement is uploaded by the IMD.

13. The temperature sensor of claim 12, wherein the scaler is implemented using a processor configured to perform an equation or use a look up table (LUT) to produce the temperature measurement based on the digital value corresponding to the duty cycle (dc) indicative of the ΔVBE.

14. The temperature sensor of claim 12, wherein the diode device and the sigma-delta modulator are components of an integrated circuit (IC) temperature sensor configured to be calibrated using a single calibration temperature measurement obtained using the IC temperature sensor while the IC temperature sensor is in a location having a known temperature that is outside a specified temperature range of interest.

15. The temperature sensor of claim 14, wherein the IC temperature sensor is configured to produce the temperature measurement such that it is within +/−0.1° C. of an actual temperature.

16. The temperature sensor of claim 9, wherein the diode device comprises a bipolar junction transistor (BJT) having a base, an emitter, and a collector, with the base and the collector connected to one another so that the diode device comprises a diode connected transistor.

17. The temperature sensor of claim 9, wherein:
based on an output of the 1-bit quantizer, a voltage equal to either C1*ΔVBE or −C1*VBE1 is selectively transferred from the capacitor, which is part of both the integrator and the 1-bit DAC of the sigma-delta modulator, to a further capacitor of the integrator,
where C1 is the value of the capacitor that is part of both the integrator and the 1-bit DAC of the sigma-delta modulator.

18. A method for producing a temperature measurement for use in an implantable medical device (IMD), the method comprising:
alternating between producing a first base-to-emitter voltage drop (VBE1) and a second base-to-emitter voltage drop (VBE2);

alternating between using a capacitor to store the VBE1, which is complimentary to absolute temperature (CTAT), and using the same capacitor to store a ΔVBE=VBE2−VBE1, which is proportion to absolute temperature (PTAT);

using a sigma-delta modulator that includes the capacitor to produce a signal having a duty cycle (dc) indicative of the ΔVBE stored using the capacitor; and producing a temperature measurement based on the signal having the duty cycle (dc) indicative of the ΔVBE;

wherein the sigma-delta modulator includes a summing node, an integrator, a 1-bit quantizer, and a 1-bit digital-to-analog converter (DAC), the integrator including an operational amplifier (op-amp) having first and second inputs and an output, with one of the first and second inputs coupled to the summing node, and the integrator also including a switch between the output of the op-amp and an input of the 1-bit quantizer;

wherein the same capacitor that is used to store both the VBE1 and the ΔVBE is part of both the integrator and the 1-bit DAC of the sigma-delta modulator; and wherein the method includes controlling the switch to selectively couple the output of the op-amp to the input of the 1-bit quantizer.

19. The method of claim 18, wherein:

the summing node is coupled to a terminal of the diode device that alternately produces the VBE1 and the VBE2;

the signal having the duty cycle (dc) indicative of the ΔVBE is output by the 1-bit quantizer; and the VBE1 that is stored on the capacitor is also used as a reference voltage for the 1-bit DAC, thereby eliminating a need for a separate reference voltage to be trimmed and used as the reference voltage for the 1-bit DAC.

20. The method of claim 19, wherein the producing the temperature measurement, based on the signal having the duty cycle (dc) indicative of the ΔVBE, comprises:

filtering the signal having the duty cycle (dc) indicative of the ΔVBE to thereby produce a digital value corresponding to the duty cycle (dc) indicative of the ΔVBE; and scaling the digital signal to produce the temperature measurement, which is within +/−0.1° C. of an actual temperature;

wherein a digital correction can be applied to the temperature measurement resulting from the scaling, with the digital correction performed by IMD, or by an external device to which the temperature measurement is uploaded by the IMD.

21. The method of claim 18, wherein the sigma-delta modulator is part of an integrated circuit (IC) temperature sensor, and wherein the method further comprises:

producing a single calibration temperature measurement using the IC temperature sensor while the IC temperature sensor is in a location having a known temperature; and performing a single point calibration of the IC temperature sensor using the single calibration temperature measurement.

22. The method of claim 21, wherein:

the IC temperature sensor is for use within a specified temperature range of interest; and the known temperature, of the location where the IC temperature sensor is located when the single calibration temperature measurement is produced, is outside the specified temperature range of interest, and thus, the single calibration temperature measurement used for the single point calibration is outside the specified temperature range of interest.

23. The method of claim 18, wherein the using the sigma-delta modulator that includes the capacitor to produce the signal having the duty cycle (dc) indicative of the ΔVBE stored using the capacitor includes:

based on an output of the 1-bit quantizer, selectively transferring a voltage equal to either C1*ΔVBE or −C1*VBE1 from the capacitor, which is part of both the integrator and the 1-bit DAC of the sigma-delta modulator, to a further capacitor of the integrator, where C1 is the value of the capacitor that is part of both the integrator and the 1-bit DAC of the sigma-delta modulator.

* * * * *